(12) United States Patent
Magnusson et al.

(10) Patent No.: US 6,462,253 B1
(45) Date of Patent: Oct. 8, 2002

(54) ABSORBENT PRODUCT COMPRISING AT LEAST ONE THERMOPLASTIC COMPONENT TO BOND LAYERS

(75) Inventors: Ing-Britt Magnusson, Mölnlycke; Peter Hedenberg, Göteborg, both of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/806,306

(22) PCT Filed: Oct. 1, 1999

(86) PCT No.: PCT/SE99/01738

§ 371 (c)(1),
(2), (4) Date: Mar. 29, 2001

(87) PCT Pub. No.: WO00/19957

PCT Pub. Date: Apr. 13, 2000

(30) Foreign Application Priority Data

May 10, 1998 (SE) ............................................... 9803356

(51) Int. Cl.[7] .................................................. A61F 13/15
(52) U.S. Cl. ..................... 604/378; 604/365; 604/370; 604/384; 604/385.23
(58) Field of Search ................................. 604/378, 365, 604/370, 375, 385.23

(56) References Cited

U.S. PATENT DOCUMENTS

| 4,397,644 A | * | 8/1983 | Matthews et al. | ............ 604/378 |
|---|---|---|---|---|
| 4,636,209 A | * | 1/1987 | Lassen | ............ 604/378 |
| 4,798,603 A | | 1/1989 | Meyer et al. | |
| 5,242,435 A | * | 9/1993 | Murji et al. | |
| 5,631,078 A | * | 5/1997 | Ellery et al. | ............ 428/311.71 |
| 5,733,273 A | * | 3/1998 | Ahr | ............ 604/378 |

FOREIGN PATENT DOCUMENTS

| EP | 0 685 214 | 12/1995 |
|---|---|---|
| GB | 2 114 445 | 8/1983 |
| WO | 97/02133 | 1/1997 |
| WO | 99/49825 | 10/1999 |

* cited by examiner

*Primary Examiner*—Rodney M. Lindsey
*Assistant Examiner*—Angela J Grayson
(74) *Attorney, Agent, or Firm*—Burns, Doane, Swecker & Mathis, L.L.P.

(57) ABSTRACT

An absorbent product comprising a liquid-permeable casing layer (402), a liquid-barrier layer (413) and an absorption element (416) which is enclosed between the liquid-permeable casing layer (402) and the liquid-barrier layer (413), and a liquid-transfer layer (403) which is disposed between the liquid-permeable casing layer (402) and the absorption element (406). The envelope layer (402) is bonded in a pattern of distinct thermally produced bonds (405) to the liquid-transfer layer (403). The liquid-transfer layer (403) comprises 40–65% by weight network-creating function fibres which are substantially intact following the bonding-together of the envelope layer (402) and the liquid-transfer layer (403) and which have a fibre coarseness ranging from 6 denier to 12 denier and 35–60% by weight fibres comprising a weldable, thermoplastic component and having a fibre coarseness of at least 3 denier.

12 Claims, 3 Drawing Sheets

ABSORBENT PRODUCT COMPRISING AT LEAST ONE THERMOPLASTIC COMPONENT TO BOND LAYERS

This application is a national stage filing under 35 U.S.C. 371 of International Application No. PCT/SE99/01738, filed on Oct. 1, 1999, and which was published in English on Apr. 13, 2000.

TECHNICAL FIELD

The invention relates to an absorbent product comprising a liquid-permeable casing layer, a liquid-barrier layer and an absorption element which is enclosed between the liquid-permeable casing layer and the liquid-barrier layer, and a liquid-transfer layer which is disposed between the liquid-permeable casing layer and the absorption element, the casing layer being bonded in a pattern of distinct bonds to the liquid-transfer layer and both the liquid-permeable casing layer and the liquid-transfer layer comprising at least one thermoplastic component and the bonds between the envelope layer and the liquid-transfer layer being thermally produced.

BACKGROUND

A liquid-permeable surface layer for an absorbent product such as a nappy, an incontinence pad, a sanitary towel or the like must rapidly admit liquid to an absorption element disposed inside the surface layer. It is additionally highly desirable that the surface layer should feel dry against the skin of the user after the product has absorbed liquid and further that liquid which has passed into the absorption element should be prevented from running back out of the product.

In order to produce a surface layer having high liquid admissibility, high surface dryness following wetting and the capacity to prevent re-wetting, it has been proposed to use surface layers which comprise thermally bonded laminates of an upper liquid-receiving layer and a lower liquid-transfer and insulating layer. Such surface-layer laminates are described in SE 9801038-2, EP 0,685,214 and WO 97/02133.

A problem associated with the previously known surface-layer laminates has proved to be however that it has not been possible simultaneously to achieve good weldability in the integral material layers, high surface dryness in the laminate and good liquid-transferability between the surface-layer laminate and an absorption element connected thereto.

The reason why the liquid-transferability between the surface layer and the absorption element has been lower than expected is that when the material layers are bonded together in the lamination process the material is squeezed together in the bonding regions, thereby forming compressed bonding regions with cushion-like, unbonded regions in between. When such a surface-layer laminate is placed on an absorption element, only the cushion-like regions between the bonding regions will be in direct contact with the absorption element, whilst gaps are formed between the surface-layer laminate and the absorption element at the bonding points. This means that liquid transfer in and immediately around the bonding regions is lower than within those cushion-like sections of the surface-layer laminate which are in direct contact with the absorption element. There is therefore a considerable risk that liquid which meets the surface-layer laminate will not be passed on to the absorption element but instead remains in the fibre structure in and around the bonding regions. Even if liquid is transferred between the surface-layer laminate and the absorption element, the transfer at the bonding locations is effected so slowly that the surface-layer laminate stays wet for a long time and in the worst case have not been able to be drained of liquid before the next quantity of liquid meets the absorbent product.

OBJECTS OF THE INVENTION

One object of the invention is to make available an absorbent product having a surface layer consisting of a laminate which has high liquid-permeability, high surface dryness and a good capacity to resist re-wetting.

A further object of the invention is to offer a surface-layer laminate comprising a liquid-transfer layer having improved weldability.

BRIEF DESCRIPTION OF THE INVENTION

A product realized according to the invention and of the type mentioned in the introduction is primarily characterized in that the liquid-transfer layer comprises 40–65% by weight of network-creating function fibres which are substantially intact following the bonding-together of the casing layer and the liquid-transfer layer and which have a fibre coarseness ranging from 6 denier to 12 denier and 35–60% by weight thermoplastic fibres comprising a weldable component and having a fibre coarseness of at least 3 denier.

According to one embodiment of the invention, the thermoplastic fibres comprise two different types of fibres in which the first fibre type provides weldability and accounts for 25–35% by weight of the liquid-transfer layer and the second fibre type is a bonding fibre and accounts for 25–35% by weight of the liquid-transfer layer. The first fibre type has a fibre coarseness of at least 3 denier and the second fibre type has a fibre coarseness of at least 4 denier.

The fibres in the liquid-transfer layer can be in the form of an essentially homogeneous mixture.

Alternatively, the weldable thermoplastic fibres can be substantially arranged as a part-layer forming part of the liquid-transfer layer. In this case the liquid-transfer layer comprises a first part-layer which comprises the network-creating fibres and a second part-layer which comprises the weldable thermoplastic fibres.

The network-creating fibres can be hollow fibres, solid fibres or spiral fibres. If spiral fibres are used, they should be chosen such that the degree of spiralling is relatively low. If the degree of spiralling is too high, there is namely a risk that too many fine capillaries will be formed in the liquid-transfer layer, which has an adverse effect upon the dryness of the layer and should therefore be avoided.

The thermoplastic fibres forming part of the liquid-transfer layer can comprise bicomponent fibres.

It has been shown that the composition of the liquid-transfer layer is critical to the bonding result and the functioning of the finished surface-layer laminate. One difficulty is to produce a weldable liquid-transfer layer which offers high surface dryness when it forms part, as a component, of a surface-layer laminate. In this context, it has been shown to be of great importance that the presence of thin fibres should be low in the cushion-like areas between the bonds. Thin fibres tend to produce a fine-capillary fibre structure which retains liquid instead of passing it on through the liquid-transfer layer to an inner absorbent structure.

It is therefore important that the liquid-transfer layer should contain sufficient quantity of weldable fibres to enable thermal bonding-together with an casing layer. It is additionally important that the proportion of thin fibres should not be so high that liquid remains in the fibre structure and makes the surface-layer laminate feel soggy and uncomfortable after wetting.

The fibres in the liquid-transfer layer have to fulfil three main functions. The liquid-transfer layer must therefore contain:

1) Function fibres, which create a network which ensures that the surface-layer laminate can admit liquid. The function fibres remain substantially unaffected by the production process and are therefore essentially intact even after welding, gluing and compression. The function fibres are resilient fibres which lend a certain thickness and volume to the wadding layer and counter act the formation of fine capillaries. Suitable function fibres can be hollow fibres, spiral fibres or solid fibres. If spiral fibres are used, it is important that these should not be so heavily spiralled that fine capillaries are formed. The fibres should have a coarseness ranging from 6 denier to 12 denier. Suitable materials are polyester or other fibres which are not weldable at the temperatures which are used to weld together the liquid-transfer layer with a liquid-permeable casing layer. The function fibres must also withstand, for example, thermal bonding of a fibre gauze during production of the liquid-transfer layer before this is welded together with the liquid-permeable casing layer. This means that either the fibres are not thermoplastic or they have a melting point above the temperature which is used in thermobonding and welding.

2) Welding fibres, which are used to bond together the fibre wadding with an casing layer. The welding fibres must give well-defined, distinct weld bondings. As welding fibres can be used, for example, bicomponent fibres having a polypropylene outer envelope and a polyester core and having a fibre coarseness of 3 denier.

3) Bonding fibres, which are used to bond a fibre gauze thermally to an associated wadding. The bonding fibres can be the same type of fibres as the welding fibres. The bonding fibres thus expediently consist of thermoplastic material or are made up of bicomponent fibres in which a superficially located component in the fibre is thermoplastic. The bonding fibres can, for example, be fibres having a co-polyester sheath and a polyester core, in which the sheath has a lower melting point than the core. Should the wadding be bonded by weeding, then there is of course no need for bonding fibres.

From the functional aspect, there have proved to be certain advantages associated with choosing the same type of fibres both as welding fibres and bonding fibres. Firstly, it is simpler to produce a wadding having only two components, secondly, it has been shown that a dual-component wadding feels drier than a triple-component wadding. This is probably due to the fact that more fine capillaries are formed in a triple-component system that in a dual-component system. A fibre which has been shown to function well both as a bonding fibre and as a welding fibre is a bicomponent fibre having a polyethylene outer sheath and a polypropylene core and having a fibre coarseness of 3 denier.

One difficulty has however been to produce fibres which function both as welding fibres and bonding fibres. For this reason, the functions can be separated into bonding and welding, resulting in a triple-component wadding.

In order to increase the dryness of the wadding when it is used as a liquid-transfer layer in a surface-layer laminate, it is expedient in a triple-component system to use relatively coarse bonding fibres and/or welding fibres. It has here been shown that a fibre coarseness of from 4 to 6 denier gives good results with regard to dryness.

Another way of achieving good weldability without the need to resort to a triple-component system is to arrange the welding fibres in a separate welding layer. A part-layer comprising function fibres and possibly also bonding fibres is in this case laminated to a part-layer essentially consisting only of welding fibres. As welding layer, a non-woven layer consisting holly or predominantly of polypropylene fibres can herein be used.

Sensory Determination of Surface Dryness

Surface dryness is a subjective property of a surface material. Quantitative measurements, for example of re-wetting and residual liquid in a surface material, therefore provide no reliable information on how the material will be perceived during use.

In order to decide whether a surface material feels wet, the material can be tested on a sensory basis by a test panel. Such a test panel consists of at least 10 test subjects.

In order to avoid disturbances, it is important that the tests should be carried out in a peaceful and harmonic environment with as few external stimuli as possible.

The test subjects are presented with two samples at a time and are given the task of judging the samples by simultaneously feeling both samples and indicating which sample feels wettest or coldest, A comparison can be made of samples having the same surface material but to which different quantities of liquid have been added, as well as of samples to which liquid has been delivered two or more times. It is also possible to compare the dryness for different types of surface material. The samples in each study are ranked by comparing the number of times a certain sample has been judged to be wetter than another sample.

BRIEF DESCRIPTION OF FIGURES

The invention shall be described in greater detail below with reference to the figures which are shown in the appended drawings, in which.

DESCRIPTION OF EMBODIMENTS

Figure 1:
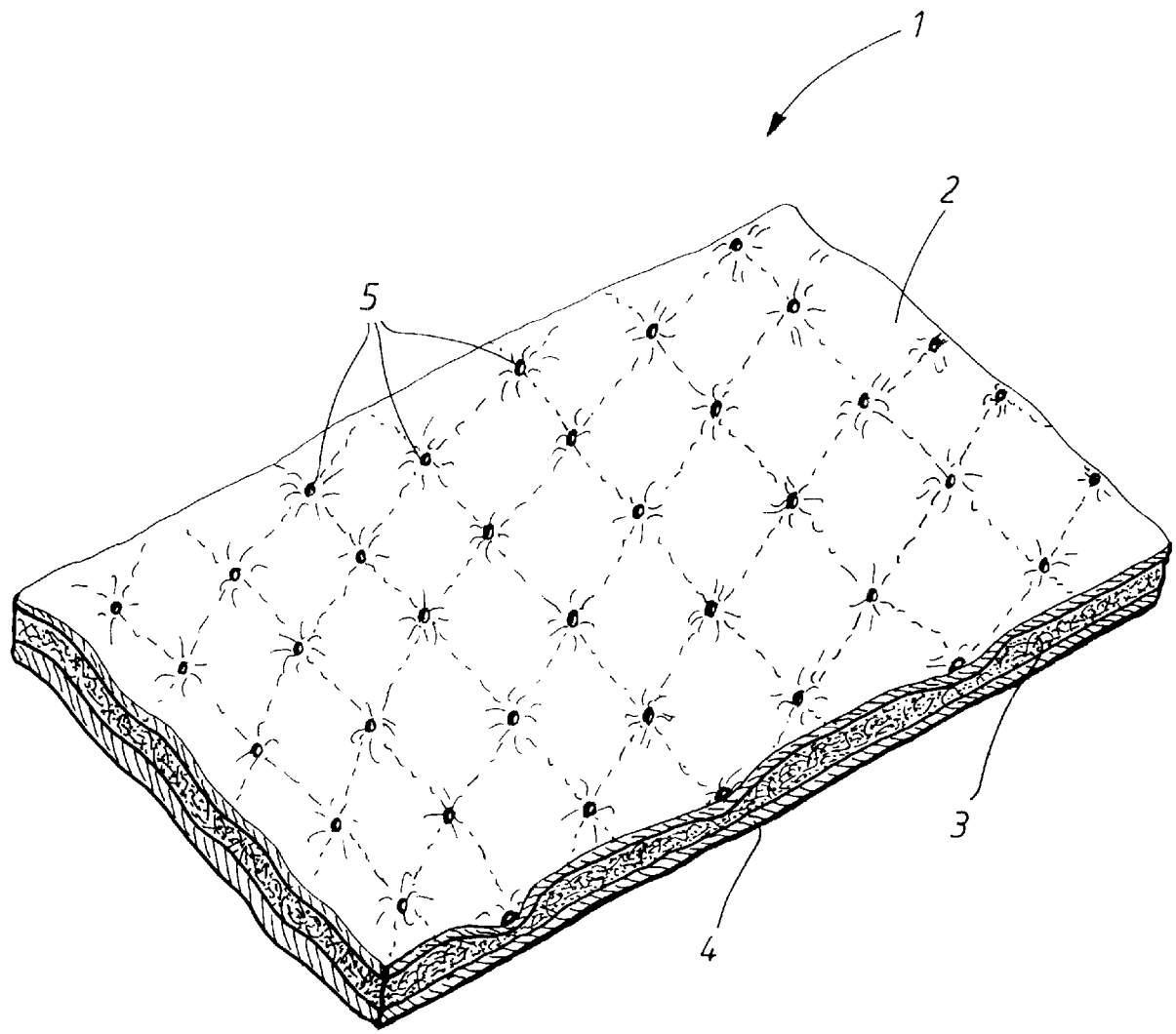
FIG. 1 shows a thermally bonded surface-layer laminate.

The surface-layer laminate shown in FIG. 1 comprises a liquid-permeable casing layer 2, a liquid-transfer layer 3 and a base layer 4.

The casing layer can be made from any material which is conventionally used as liquid-permeable outer casing on absorbent products. The casing layer 2 can thus be made up of a perforated plastic film, a plastic or textile material net or a non-woven layer. The casing layer preferably contains some thermoplastic component such as polyethylene, polyester or polypropylene. The thermoplastic component expediently accounts for at least 30 percent by weight of the casing layer 2, since the bonding-together of the casing layer 2 and the underlying liquid-transfer layer 3 is facilitated when both layers 2, 3 contain thermoplastic material. A casing layer made from non-woven material can additionally contain natural fibres, such as cellulose or cotton, or non-thermoplastic synthetic fibres, such as polyurethane, nylon or regenerated cellulose.

The liquid-transfer layer 3 is a fibre wadding layer and constitutes a spacing means between the casing layer 2 and an underlying layer, in the figure the base layer 4. When the surface-layer laminate 1 is used as the liquid-permeable outer layer on an absorbent product, the distance-creating capacity of the liquid-transfer layer helps to keep liquid which has been absorbed into an absorption element integral to the product at a distance from the body of the user and prevents absorbed liquid from running back out from the absorption element. The liquid-transfer layer 3 further has the capacity to mask or disguise liquid which has been absorbed by the absorption element. The fact that the fibre-wadding layer is soft, volume-creating and springy also produces good user comfort.

The base layer 4 is a stabilising layer which is used to increase the tensile strength of the liquid-transfer layer 3. Such a stabilising layer can be usable where the liquid-transfer layer 3 is a layer of needled wadding. Suitable base layers are different types of non-woven materials. One example of a non-woven material which has been found to work well as a base layer for needled wadding layers is a carded non-woven made from polypropylene fibres. The base layer 4 is not necessary to the invention but can be excluded. Where the liquid-transfer layer 3 is a wadding layer with sufficient inherent tensile strength to be able to be used in a production process, there is obviously no need for a base layer.

The surface-layer laminate 1 further has a multiplicity of discrete welding spots or thermal bondings 5, which form well-like recesses on that surface of the surface-layer laminate 1 on which the casing layer 2 is disposed.

Figure 2:
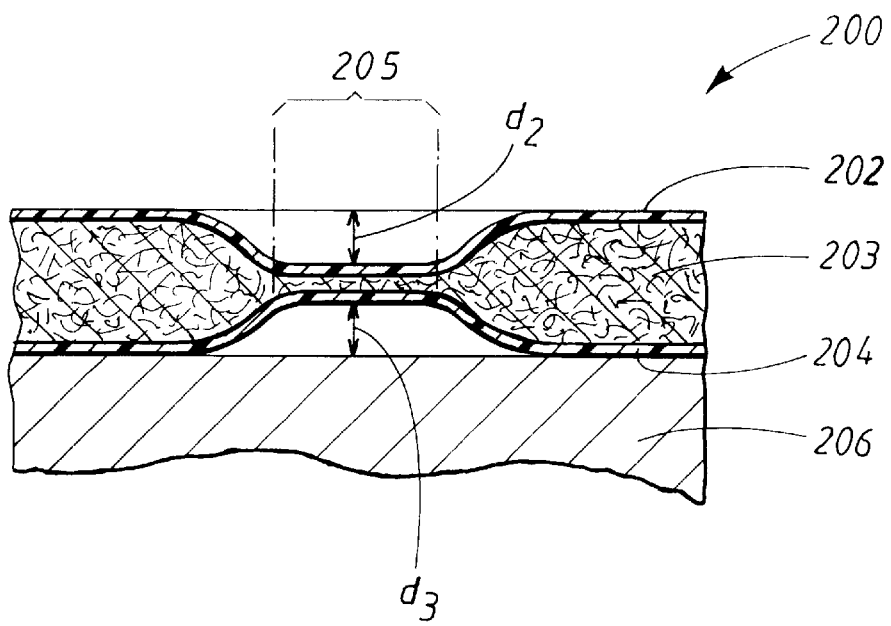
FIG. 2 shows a section through a surface-layer laminate according to the prior art.

FIG. 2 shows in cross section a surface-layer laminate 200 according to the prior art. Like the surface-layer laminate 1 in FIG. 1, the surface-layer laminate 200 comprises a liquid-permeable casing layer 202, a liquid-transfer layer 203 and a base layer 204. The surface-layer laminate 200 is disposed on a layer of absorption material 206, which is intended to absorb liquid which passes in through the surface-layer laminate 200.

The shown section of the surface-layer laminate 200 comprises a welding spot 205. As can be observed in the figure, the welding spot 205 is situated at a distance $d_2$ from that surface of the liquid-permeable casing layer 202 facing away from the liquid-transfer layer 203 and at a distance $d_3$ from the absorption layer 206. This means that liquid which collects in the depressions at the welding spots 205 risks being caught in the liquid-transfer layer 203 since the gap $d_3$ between the welding spots 205 and the absorption layer 206 constitutes an obstacle to the flow of liquid.

Figure 3:
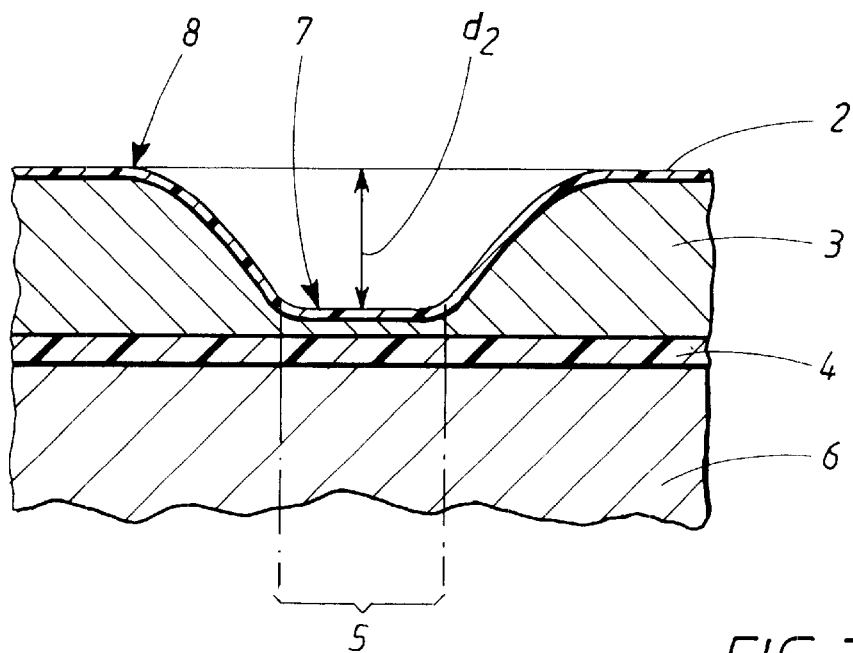
FIG. 3 shows a section through a surface-layer laminate according to the invention.

FIG. 3 shows a section through a welding spot 5, in the surface-layer laminate 1 according to the invention shown in FIG. 1, when the surface-layer laminate is disposed on an absorption layer 6. In the welding spot 5 the material layers 2-4 integral to the surface-layer laminate are pressed together, with a degree of compression which decreases in the direction away from the welding spot 5. The liquid-transfer layer 3 has a pore gradient around the welding spots 5, the pores being at their minimum directly alongside each welding spot and increasing to a maximum value corresponding to the pore size in those parts of the liquid-transfer layer 3 which have no welding spots 5. The upper surface 7 of the welding spot 5, i.e. that surface which, during use, is intended to be facing towards a user, is depressed by a distance $d_2$ from that surface 8 of the liquid-permeable casing layer 2 facing away from the liquid-transfer layer 3. The fact that the fibre composition in the liquid-transfer layer is such that the liquid-transfer layer 3 has extremely good weldability properties has the result that no play is formed between the surface-layer laminate 1 and the underlying absorption layer 6. This means that the liquid transfer between the surface-layer laminate 1 and the absorption layer is very good and that an absorbent product provided with a surface-layer laminate 1 according to the invention has a dry, comfortable surface, even after wetting.

The fact that the distance $d_2$ accounts for a greater share of the combined thickness of the surface-layer laminate 1 than had previously been possible to produce when welding together a liquid-transfer layer 3 with a liquid-permeable casing layer 2 results in a more pronounced pore gradient being obtained around the welding spots 5 and hence improved liquid transport in through the surface-layer laminate 1. For a surface-layer laminate according to the invention, the distance $d_2$ preferably accounts for at least 60% and ideally at least 75% of the combined thickness of the surface-layer laminate. In certain cases the welding spots 5 can have continuous openings or perforations, which means that the distance $d_2$ accounts for 100% of the combined thickness of the surface-layer laminate 1.

As previously mentioned, it is possible to separate the components in the liquid-transfer layer 3 so that the weldable fibres are disposed in a separate layer. By way of alternative, FIG. 3 shows an embodiment of this kind in which the weldable thermoplastic fibres are disposed in the base layer 4, which in this case constitutes a welding layer 4. The liquid-transfer layer 3 can here be constituted, for example, by a needled wadding or by a wadding which has been bonded using some other method suitable for the purpose. In the welding-together of the liquid-permeable casing layer 2 and the liquid-transfer layer 3, the bonding is effected by melting of the fibres in the welding layer 4.

Figure 4:
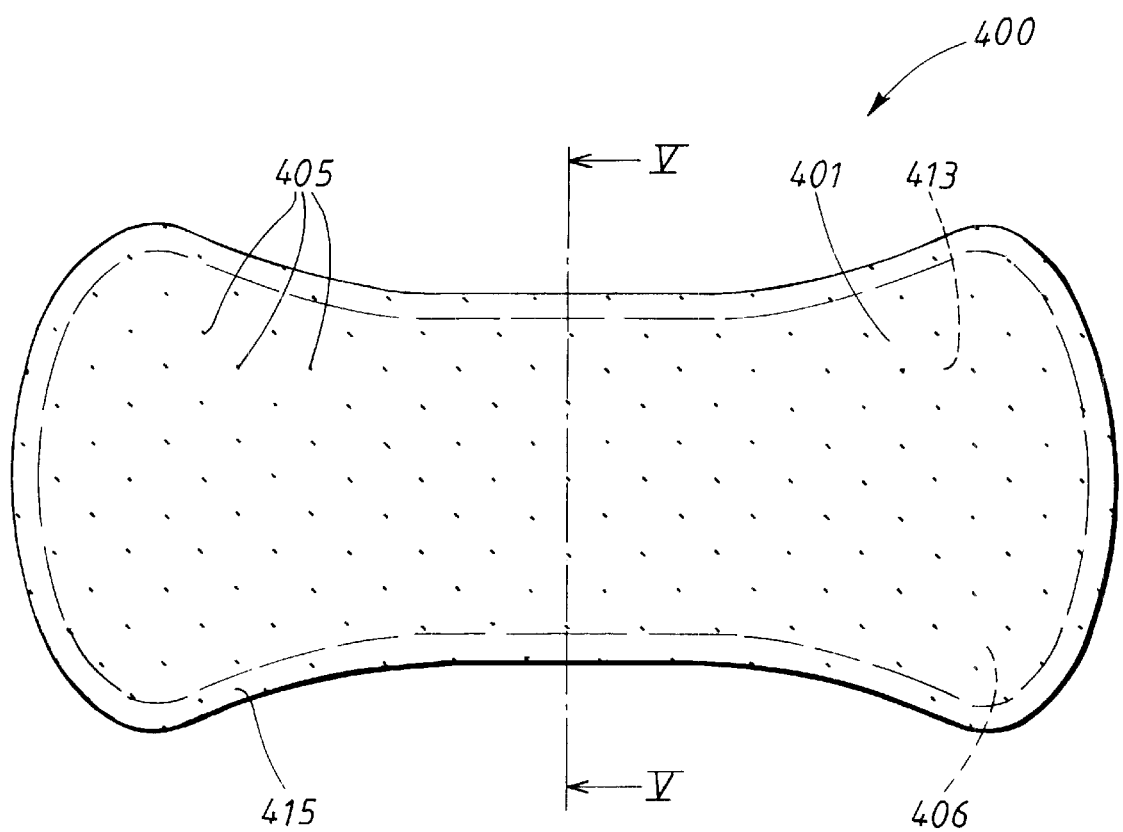
FIG. 4 shows a planar view of an incontinence pad having a surface-layer laminate according to the invention.
Figure 5:
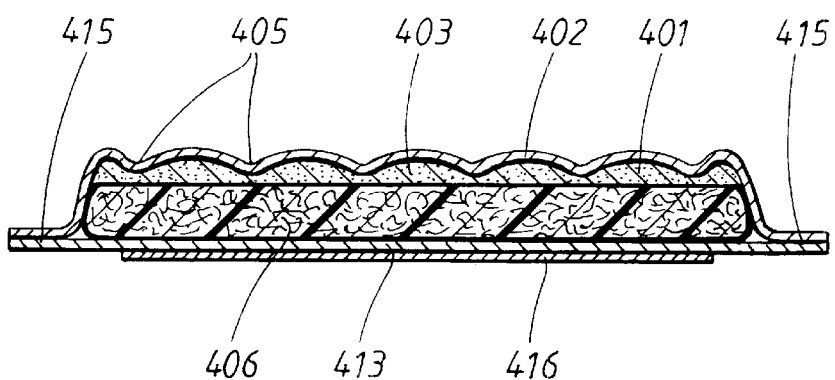
FIG. 5 shows a section along the line V—V through the incontinence pad in FIG. 4.

The incontinence pad 400 shown in FIGS. 4 and 5 comprises a liquid-permeable surface-material laminate 401 disposed on that side of the incontinence pad 400 which, during use, is intended to be facing towards the user, a liquid-tight envelope layer 413 disposed on that side of the incontinence pad which, during use, is intended to be facing away from the user and an absorption element 406 enclosed between the surface-material laminate 401 and the liquid-tight envelope layer 413.

The surface-material laminate 401 comprises a liquid-permeable envelope layer 402 and a liquid-transfer layer 403, which are bonded together with a multiplicity of punctual welding spots 405.

The liquid-tight envelope layer 413 can conventionally consist of a liquid-tight plastic film, a non-woven layer which has been coated with a liquid-blocking material, or some other flexible material layer which has the capacity to resist liquid penetration. It can be an advantage if the liquid-tight envelope layer 413 has a certain breathability, i.e. allows the passage of water vapour through the layer 413. The liquid-tight casing layer 413 and the surface material laminate 401 have somewhat larger extent in the plane than the absorption element 406 and extend a little way out past the absorption element 406 around the whole of the periphery of the latter. The surface-material laminate 401 and the liquid-tight envelope layer 413 are mutually joined within the protruding sections 415, for example by means of gluing or thermal or ultrasound welding.

As can be seen from FIG. 5, the liquid-transfer layer 403 extends only over the surface of the absorption element 406, whilst the liquid-permeable casing layer 402 alone reaches out into the edge joints 415. Such an embodiment is not of course necessary to the invention, but rather the liquid-transfer layer 403 can have the same extent in the plane as the liquid-permeable casing layer 402. Alternatively, the liquid-transfer layer 403 can be disposed only over a longitudinal central section of the absorption element 406.

As a result of the advantageous composition of fibres in the liquid-transfer layer 403, the liquid-transfer layer 403 and the liquid-permeable casing layer 402 were able to be welded together in such a way that that surface of the resultant surface-layer laminate 1 which bears against the absorption element 406 is essentially smooth. This means that there is direct contact between the surface-layer laminate 1 and the absorption element 406 over the whole of the surfaces lying one against the other, whereby liquid is able to be transported from the liquid-permeable casing layer 402 to the absorption element without any hindrance by gap at the bonding points 405.

The absorption element 406 can be of any type whatsoever which is suitable for the purpose. Examples of commonly used absorption material are cellulose fluff material, tissue layers, highly-absorbent polymers, absorbent foam materials, absorbent non-woven materials and the like.

Material mixtures and absorption bodies built up of layers of material of different types and with different properties are also found.

By highly-absorbent polymers is meant in this context polymers present in the form of fibres, particles, flakes, granulates or the like which have the capacity to absorb body liquid equivalent to many times their own dry weight, with the formation of a liquid-containing gel.

On the outside of the liquid-tight envelope layer 3 there is disposed a fastening member 416 in the form of a longitudinal region of self-adhesive glue. The fastening member 416 is expediently covered before use by a detachable protective layer (not shown in the figures) of release agent-treated paper, plastic film or the like. Instead of the shown glue pattern in the form of a longitudinal glue region, other glue patterns can of course be used such as transverse bands, dots, full-coating, etc. Alternatively other types of fastening member can be utilized, such as hook and loop surfaces, snap fasteners, girdles, special briefs or the like.

An incontinence pad 400 of the type shown is primarily conceived for use by persons with relatively mild incontinence problems and is therefore of such a size that it can comfortably be accommodated inside a pair of ordinary briefs. The fastening member 416 serves during use to keep the incontinence pad in place inside the briefs.

It is obviously possible to use other types of welding patterns than the spot-welding pattern which has been shown in the figures. Welding patterns in the form of continuous or broken lines, such as circles, triangles, flowers, etc., can thus be used. Especially preferred welding patterns are those which are described in Swedish patent application SE 9801038-2.

Even though the surface-material laminate according to the invention in the example shown in FIGS. 4 and 5 is used as the liquid-permeable surface layer on an incontinence pad, this shall not of course be considered limiting for the invention. A surface-material laminate according to the invention can thus be used on all types of product which are intended for absorption of body liquids. Examples of such products are nappies for adults and children, bed and seat protection, sanitary towels, party liners and absorbent bandages.

What is claimed is:

1. An absorbent product comprising a liquid-permeable casing layer, a liquid-barrier layer and an absorption element which is enclosed between the liquid-permeable casing layer and the liquid-barrier layer, and a liquid-transfer layer which is disposed between the liquid-permeable casing layer and the absorption element, the casing layer being bonded in a pattern of distinct bonds to the liquid-transfer layer and both the liquid-permeable casing layer and the liquid-transfer layer comprising at least one thermoplastic component and the bonds between the casing layer and the liquid-transfer layer being thermally produced, characterized in that the liquid-transfer layer comprises 40–65% by weight network-creating function fibres which are substantially intact following the bonding-together of the casing layer and the liquid-transfer layer and which have a fibre coarseness ranging from 6 denier to 12 denier and 35–60% by weight thermoplastic fibres comprising a weldable component and having a fibre coarseness of at least 3 denier.

2. An absorbent product according to claim 1, in which the liquid-transfer layer comprises two different types of thermoplastic fibres in which a first fibre type is weldable and accounts for 25–35% by weight of the liquid-transfer layer and the second fibre type serves as bonding fibres and accounts for 25–35% by weight of the liquid-transfer layer and in which the first fibre type has a fibre coarseness of at least 3 denier and the second fibre type has a fibre coarseness of at least 4 denier.

3. An absorbent product according to claim 1, in which the fibres in the liquid-transfer layer are in the form of an essentially homogenous mixture.

4. Absorbent product according to claim 1, in which the liquid-transfer layer comprises a first part-layer comprising the network-creating fibres and a second part-layer which comprises the weldable thermoplastic fibres.

5. Absorbent product according to claim 1, in which the intact, network-creating fibres are hollow fibres.

6. Absorbent product according to claim 1, in which the intact, network-creating fibres are solid fibres.

7. Absorbent product according to claim 1, in which the intact, network-creating fibres are spiral fibres.

8. Absorbent product according to claim 1, in which the intact, network-creating fibres comprise bicomponent fibres.

9. Absorbent product according to claim 8, in which the bicomponent fibres have a polyethylene sheath and a polypropylene core.

10. Absorbent product according to claim 1, in which the first type of thermoplastic fibres are bicomponent fibres having a polyproplene sheath and a polyester core.

11. Absorbent product according to claim 1, in which the second type of thermoplastic fibres are bicomponent fibres having a polyproplene or co-polyester sheath and a polyester core.

12. Absorbent product according to claim 1, in which bonds have an upper surface which, when the absorbent product is used, is intended to be facing towards a user and in which the upper surface is depressed by a distance $d_2$ from that surface of the liquid-permeable casing layer facing away from the liquid-transfer layer, the distance $d_2$ preferably accounting for at least 60% of the combined thickness of the surface-layer laminate.

* * * * *

UNITED STATES PATENT AND TRADEMARK OFFICE
CERTIFICATE OF CORRECTION

PATENT NO.       : 6,462,253 B1
DATED            : October 8, 2002
INVENTOR(S)      : Ing-Britt Magnusson et al.

It is certified that error appears in the above-identified patent and that said Letters Patent is hereby corrected as shown below:

<u>Title page,</u>
Please correct the Priority Data to read:
-- [30]          Foreign Application Priority Data
October 5, 1998 (SE) …………………………………….. 9803356 --

Signed and Sealed this

Nineteenth Day of August, 2003

JAMES E. ROGAN
*Director of the United States Patent and Trademark Office*